United States Patent
Wenstad (10) Patent No.: US 7,449,002 B1
(45) Date of Patent: Nov. 11, 2008

(54) STEERABLE GUIDE WIRE FOR DELIVERING AN IMPLANTABLE MEDICAL DEVICE

(75) Inventor: Hans K. Wenstad, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 217 days.

(21) Appl. No.: 11/399,787

(22) Filed: Apr. 6, 2006

(51) Int. Cl.
*A61B 5/00* (2006.01)

(52) U.S. Cl. .................................... 600/585

(58) Field of Classification Search ............. 600/585; 606/200; 604/170.01, 528, 95.04
See application file for complete search history.

(56) References Cited

U.S. PATENT DOCUMENTS

| | | | | |
|---|---|---|---|---|
| 4,998,916 A | * | 3/1991 | Hammerslag et al. | 604/528 |
| 5,060,660 A | * | 10/1991 | Gambale et al. | 600/585 |
| 5,403,297 A | | 4/1995 | Imran | 604/281 |
| 5,599,305 A | | 2/1997 | Hermann et al. | 604/95 |
| 5,824,031 A | | 10/1998 | Cookston et al. | 607/122 |
| 6,132,390 A | | 10/2000 | Cookston et al. | 600/585 |
| 7,066,946 B2 | * | 6/2006 | Douk et al. | 606/200 |
| 2004/0143197 A1 | | 7/2004 | Soukup et al. | 600/585 |
| 2005/0273020 A1 | * | 12/2005 | Whittaker et al. | 600/585 |

FOREIGN PATENT DOCUMENTS

| | | |
|---|---|---|
| EP | 0 715 865 A2 | 6/1996 |
| WO | WO 97/31677 | 9/1997 |
| WO | WO 00/22981 | 4/2000 |

* cited by examiner

*Primary Examiner*—Max Hindenburg
*Assistant Examiner*—Brian Szmal (57) ABSTRACT

A guide wire assembly for facilitating placement of a medical device comprises (a) a longitudinally extending guide wire comprising a plurality of wire portions disposed adjacent to each other, each of the plurality of wire portions having a distal extremity and a proximal extremity, the distal extremities of the plurality of wire portions being joined, and (b) an actuator operatively associated with the proximal extremities of the plurality of wire portions for applying longitudinally directed, differential push-pull forces to the proximal extremities for deflecting a distal end portion of the guide wire.

19 Claims, 12 Drawing Sheets

STEERABLE GUIDE WIRE FOR DELIVERING AN IMPLANTABLE MEDICAL DEVICE

FIELD OF THE INVENTION

The present invention relates generally to medical devices, and particularly to a steerable guide wire for facilitating the delivery of a medical device such as an intravascular lead or catheter into a target area of the body such as a vessel of the coronary sinus region of the heart.

BACKGROUND OF THE INVENTION

The advantages of providing pacing therapies to the left side heart chambers and to both the right and left heart chambers are well established. For example, in four chamber pacing systems, multiple pacing leads, typically bipolar leads, are positioned for both pacing and sensing in or on the respective heart chambers. To provide left side pacing and sensing, leads are transvenously placed in the coronary sinus region, for example, in a vein such as the great vein or the left posterior ventricular (LPV) vein proximate the left ventricle of the heart. Such placement avoids the risks associated with implanting a lead directly within the left ventricle that can increase the potential for the formation of blood clots which, if dislodged, could cause a stroke.

Figure 1:
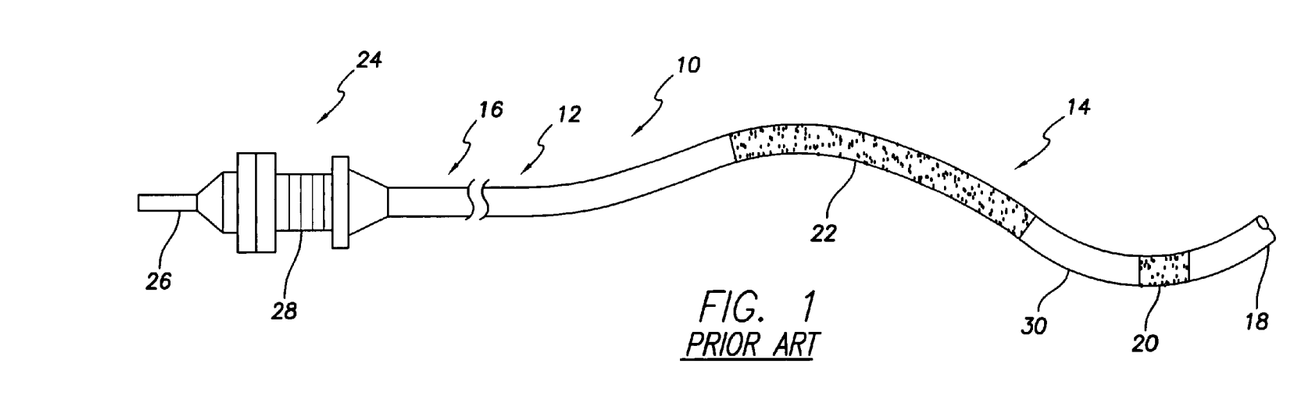
FIG. 1 is a side view of a conventional endocardial lead for placement in a vessel in the coronary sinus region of the heart.

FIG. 1 shows an example of a typical bipolar left side lead 10. The lead 10 includes a lead body 12 having a distal portion 14 and a proximal portion 16. The distal portion 14 may carry various combinations of pacing, sensing and/or defibrillation electrodes, all well-known in the art. In the specific example shown in FIG. 1, the distal portion of the lead includes a tip electrode 18 at the distal extremity of the lead body 12 for delivering electrical stimuli to selected tissue of the heart, a ring sensor electrode 20 positioned proximally of the tip electrode 18 and a shocking electrode 22 disposed proximally of the ring electrode 20. These electrodes are electrically connected to a connector assembly 24 at the proximal extremity of the lead body 12. Typically, the connector assembly 24 comprises a coaxial structure including a hollow or tubular connector pin 26 and a plurality of terminal contact rings 28. Further, as is well-known in the art, the connector assembly 24 may comprise a bifurcated or trifurcated structure depending upon the number and functions of the electrodes carried by the distal portion 14 of the lead body.

A lead such as that shown in FIG. 1, designed for placement in the coronary sinus region of the heart, will typically include an anchoring or fixation means 30. In the example under consideration, the fixation means 30 comprises one or more bends preformed along the distal portion of the lead body. As is known, with such a sinuous configuration, the bend or bends in the distal portion of the lead will press against the walls of the coronary vessel within which the distal portion of the lead is placed. The friction caused by such biasing tends to anchor or fix the distal portion of the lead body.

Presently, the distal portion of a medical lead such as that shown in FIG. 1 is maneuvered into position within a coronary vessel by means of a stylet and/or by means of a guide wire. In the latter case, an "over-the-wire" (OTW) placement technique is utilized. Such lead placement methods are well-known in the art.

The placement of a lead in the coronary sinus region is often difficult because of the extreme curvatures in the veins, their narrowness, anomalies in the vascular anatomy because of disease, and the number of veins that may communicate with the desired lead feed path. Stylets are often found to be too stiff to be easily steered within the tortuous vasculature of the coronary sinus region. Thus, a more common approach to the left side implantation of an intravenous lead is the use of a flexible guide wire over which the lead is slid to its destination. For this purpose, the lead body is typically provided with a tip electrode having a central aperture through which the guide wire can pass.

Figure 2:
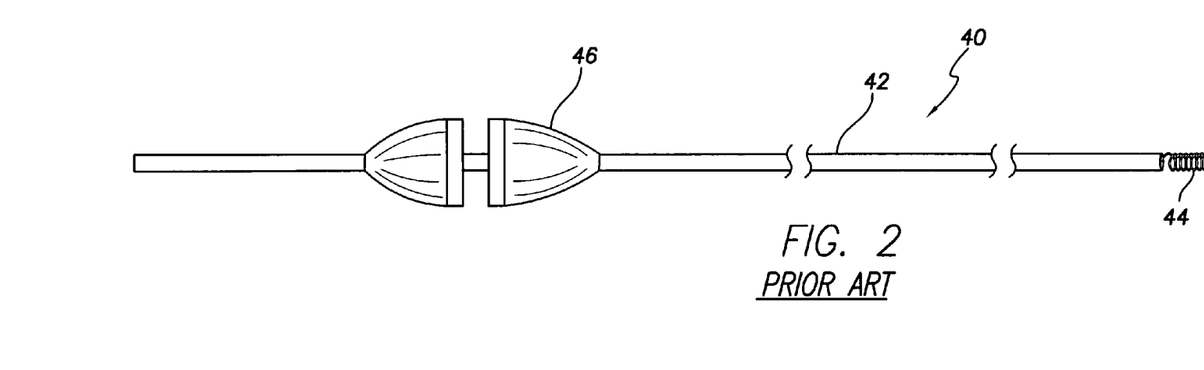
FIG. 2 is a side view of a conventional guide wire for delivering a lead such as that shown in FIG. 1 to a target vessel in the coronary sinus region.

With reference to FIG. 2, there is shown a typical guide wire 40 in present use. The guide wire 40 comprises a thin, solid wire body 42 and a flexible end 44 comprising a finely coiled structure welded to the distal extremity of the wire body 42. The guide wire is steered and its flexible end is advanced into position within the target coronary vessel using a releasable or selectively lockable clamp 46 which, when loosened, can be slid along the wire body 42 of the guide wire.

In use, the guide wire 40 is inserted into the patient's vascular system utilizing an introducer. After the flexible end of the guide wire is properly placed, the introducer is withdrawn, the clamp 46 is removed and the lead is slid over the exposed part of the guide wire and advanced "over-the-wire" into the vessels. With the distal portion of the lead in place within the target vessel, the guide wire is withdrawn. In some instances, a sheath is first routed over the guide wire to protect the walls of the vessels along the insertion path. In these cases, after the sheath is in place, the guide wire is removed and a medical device such as a lead or a catheter may then be introduced into the patient's vascular system through the sheath.

Conventional guide wires of the type described impart a degree of curvature to the distal end of the lead so as to facilitate the advancement of the lead's distal end through the tortuous paths of a patient's vascular system. To this end, if an obstacle is encountered, the guide wire is withdrawn from the lead and is given a temporary bend or curve, and then reinserted in the lumen of the lead to further advance the lead. The process of withdrawing the guide wire, rebending it (or substituting a fresh guide wire therefor) and reinserting it is repeated until the lead tip has been advanced to the target location. This conventional lead placement technique has drawbacks. For example, the guide wire can only be deflected or bent in a single direction. More importantly, repeated removal and reinsertion of the guide wire increases the risk of infection and injury to the patient in addition to being time consuming.

As an aid to efficiently and safely routing guide wires through the tortuous vasculature of the coronary sinus region, there have been developed guide wires having distal end portions deflectable in at least one direction by means of an actuating handle at the proximal end of the guide wire. There continues to be a need, however, for improvements in steerable guide wires in terms of simplicity and the range of curvatures in the deflectable distal end portion of the guide wire.

SUMMARY

In accordance with one, specific, exemplary embodiment, there is provided a guide wire assembly for facilitating placement of a medical device, the assembly comprising (a) a longitudinally extending guide wire comprising a plurality of wire portions disposed adjacent to each other, each of the plurality of wire portions having a distal extremity and a proximal extremity, the distal extremities of the plurality of wire portions being joined and (b) an actuator operatively associated with the proximal extremities of the plurality of wire portions for applying longitudinally directed, differential push-pull forces to the proximal extremities for deflecting a distal end portion of the guide wire.

In one embodiment, the distal extremities of the plurality of wire portions may be joined by a weld. In other exemplary forms of the invention, the distal extremities of the plurality of wire portions may be joined by a cap encapsulating the distal extremities or by means of a filament wound about the distal extremities.

BRIEF DESCRIPTION OF THE DRAWINGS

The foregoing and other objects, features and advantages of the invention will be evident to those skilled in the art from the detailed description below, taken together with the accompanying drawings, in which.

DETAILED DESCRIPTION

The following description includes the best mode presently contemplated for practicing the invention. This description is not to be taken in a limiting sense but is made merely for the purpose of describing the general principles of the invention whose scope may be ascertained with reference to the appended claims.

For example, it will be understood that a steerable guide wire in accordance with the invention may be used for steering any kind of medical device including, but not limited to, electrical tissue stimulation leads and endoscopic surgical instruments, within the body of a patient for placement in a target location such as, for example, the heart, bladder, lungs, and so forth.

Figure 3:
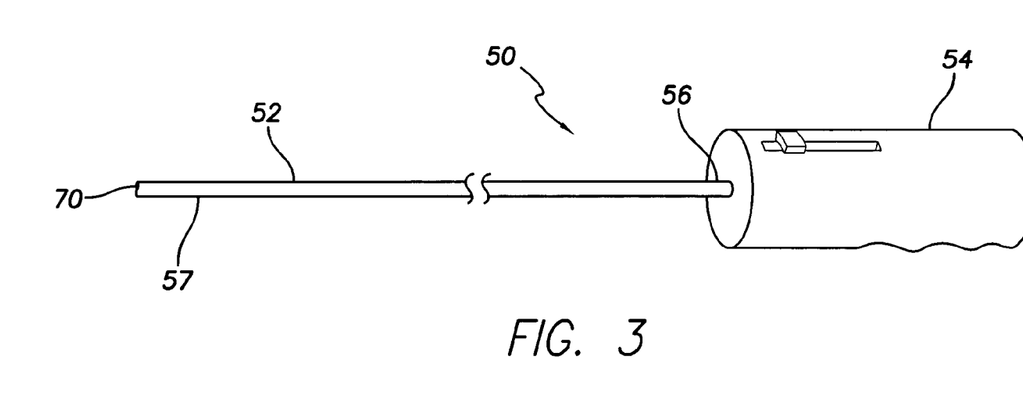
FIG. 3 is a perspective view of an assembly comprising a guide wire in accordance with one embodiment of the present invention and an actuator for deflecting or steering a distal end of the guide wire.
Figure 4:
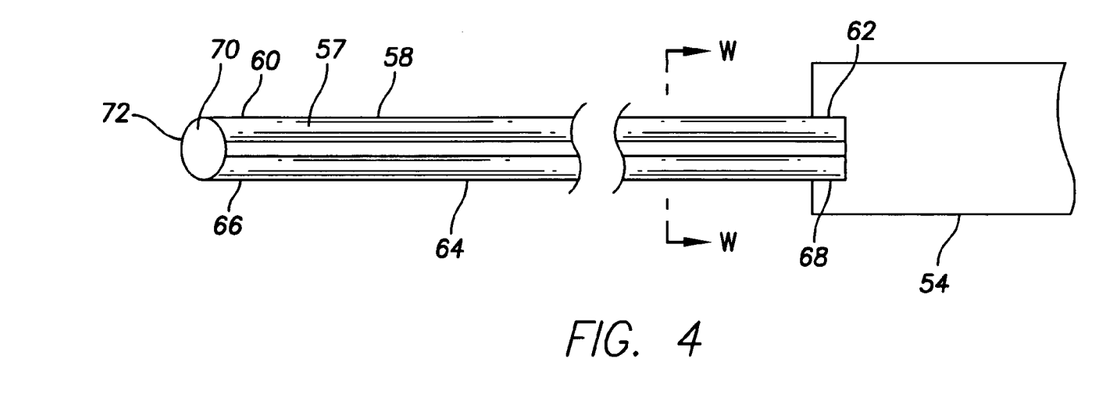
FIG. 4 is a side view showing in simplified form the assembly of FIG. 3.
Figure 5:
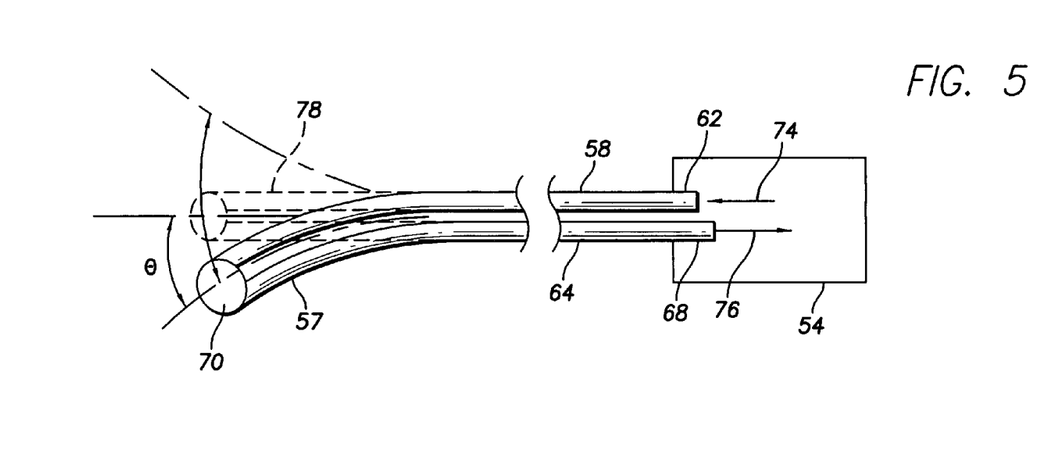
FIG. 5 is a side view of the assembly of FIG. 3 showing a distal end of the guide wire in a deflected state.

With reference to FIGS. 3-5, there is shown in schematic form an assembly 50 comprising a guide wire 52 in combination with a handle 54 at a proximal end 56 of the guide wire. The handle 54 incorporates a mechanism for deflecting a distal end portion 57 of the guide wire. Details of exemplary forms of the actuator are described below.

The guide wire 52 comprises a first wire portion 58 having a distal extremity 60 and a proximal extremity 62 and a second wire portion 64 having a distal extremity 66 and a proximal extremity 68. The first and second wire portions 58 and 64 are preferably identical in material, length and diameter and extend longitudinally in adjacent relationship; for example, the wire portions 58 and 64 may be in abutting or near abutting relationship with each other along their lengths. The distal extremities 60 and 66 of the first and second wire portions are joined together. In the embodiment of FIGS. 3-5, such joinder is effected by a weld which preferably takes the form of a bead 70 having a smooth outer surface 72. In accordance with one specific example, the first and second wire portions 58 and 64 may be formed of a biocompatible, biostable material such as stainless steel. The overall width, w (FIG. 4), of the guide wire 52 may be in the range of 0.012 to 0.016 inch in accordance with one example. Each wire portion preferably has sufficient column strength to transmit a longitudinally directed compressive force applied to the proximal extremity thereof.

As shown schematically in FIG. 5, deflection of the distal end portion 57 of the guide wire is effected by applying longitudinally directed, differential push-pull forces to the proximal extremities 62 and 68 of the first and second wire portions, respectively. For example, as shown in the drawing, a push or compressive force 74 may be applied to the proximal extremity 62 of the first wire portion 58 while a pull or tensile force 76 is applied to the proximal extremity 68 of the second wire portion 64. In response to the application of such differential forces, the distal end portion 57 of the guide wire deflects through an angle 2 as shown in FIG. 5. The extent of deflection will depend on the magnitudes of the differential forces that are applied. When inserted in a vessel of a patient's vascular system, the wall of the vessel will tend to keep the wire portions 58 and 64 in proximity to each other and resist a tendency of either or both of the wire portions to bow outwardly as a result of the application of the differential forces. In the embodiment of FIGS. 3-5, the distal end portion 57 of the guide wire may be deflected bidirectionally relative to an undeflected, relaxed state 78 shown in broken lines in FIG. 5.

Figure 6:
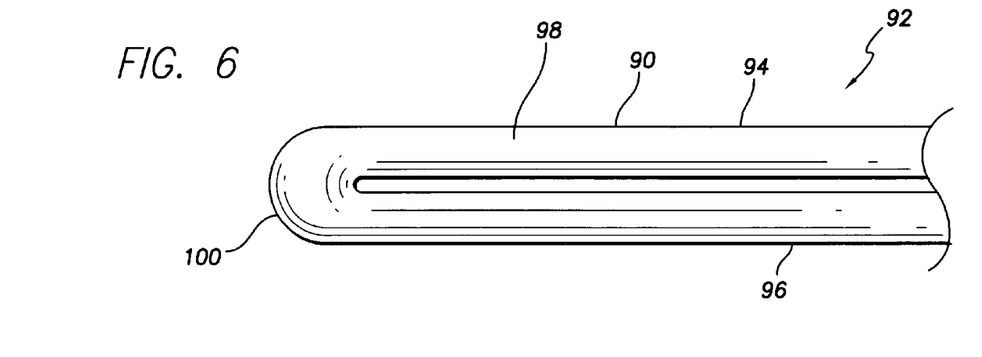
FIG. 6 is a side view of the distal end of a guide wire in accordance with an alternative embodiment of the present invention.

It will be evident that the distal extremities of the guide wire portions may be joined in any of a variety of ways. FIG. 6 shows a distal end portion 90 of a guide wire 92 comprising first and second guide wire portions 94 and 96 formed from a single wire 98 bent sharply into a U-shape defining a distal tip 100 joining, and integral with, the guide wire portions 94 and 96. The guide wire portions have proximal extremities (not shown) received by a handle incorporating a mechanism for applying differential push-pull forces to the proximal extremities, such forces deflecting the distal end portion 90 as already explained.

Figure 7:
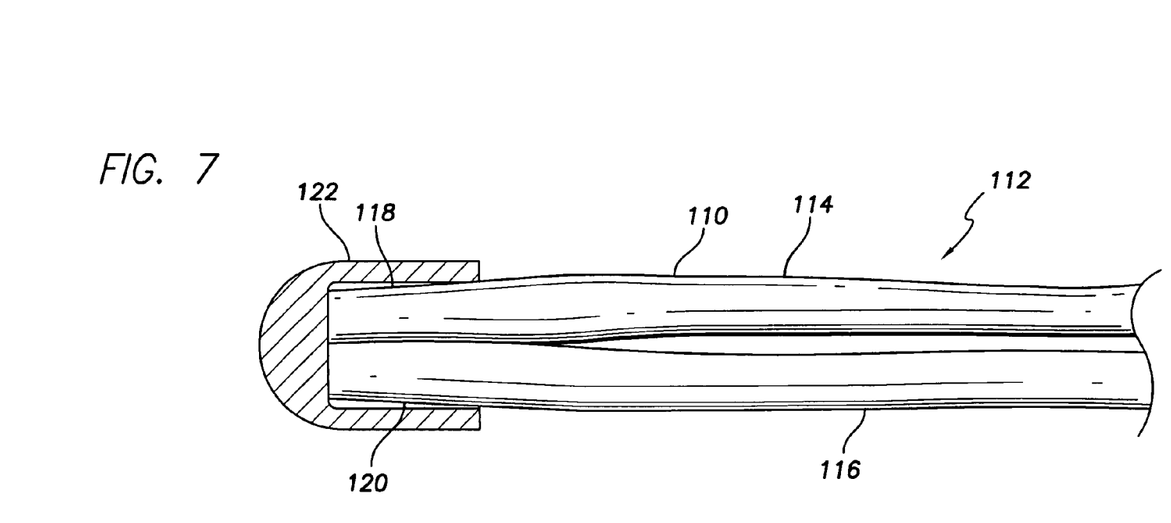
FIG. 7 is a side view of a guide wire in accordance with another alternative embodiment of the present invention.

Alternatively, FIG. 7 shows a distal end portion 110 of a guide wire 112 comprising separate first and second wire portions 114 and 116 having distal extremities 118 and 120, respectively, joined by an end cap 122 capturing the distal extremities 118 and 120 of the wire portions. The end cap 122 may be applied to the distal extremities by crimping, welding, or otherwise. As before, proximal extremities (not shown) of the guide wires respond to a push-pull actuating mechanism carried by a handle (not shown) so as to deflect the distal end portion 110 of the guide wire to an extent depending upon the magnitude of the applied differential forces.

Figure 8:
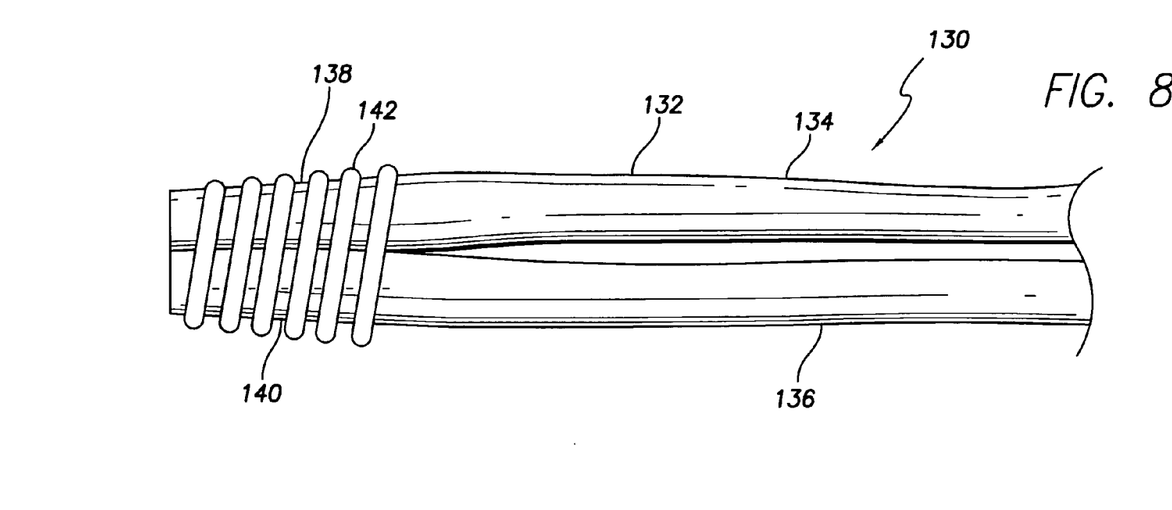
FIG. 8 is a side view of the distal end of a guide wire in accordance with yet another embodiment of the present invention.

Still further, as depicted in FIG. 8, a guide wire 130 in accordance with the invention may comprise a distal end portion 132 comprising first and second wire portions 134 and 136 having distal extremities 138 and 140 joined by wrapping them together with a metal or polymer strand or filament 142. The filament 142 is preferably bonded to the distal extremities of the wire portions by a medical adhesive in the case of a polymer filament or by a weld in the case of a metal filament. Again, the guide wire's distal end portion 132 may be deflected by a push-pull action as already described. It will be evident that the guide wire portions need not be joined precisely at their distal extremities. Thus, the wire portions may be joined at a location a short distance proximally of their distal extremities without impairing the delectability of the guide wire.

Figure 9:
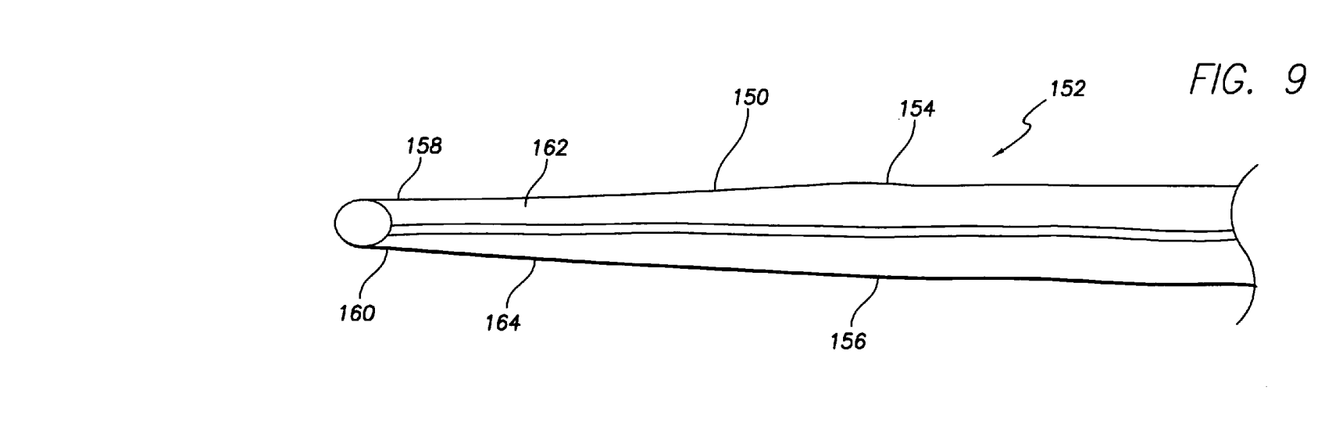
FIG. 9 is a side view of the distal end of a guide wire in accordance with a further embodiment of the present invention.

Referring to FIG. 9, there is shown a distal end portion 150 of a guide wire 152 in accordance with another embodiment of the invention. The guide wire 152 comprises a pair of guide wire portions 154 and 156 joined at their distal extremities 158 and 160. The flexibility of the deflectable distal end portion 150 of the guide wire may be increased by providing each of the wire portions 154 and 156 with a tapered configuration 162 and 164 along the distal end portion 150. Instead of a smooth taper, as shown, it will be evident that a progressive reduction in the diameters of the wire portions may be effected by forming one or more steps in the wire portions.

Figure 10:
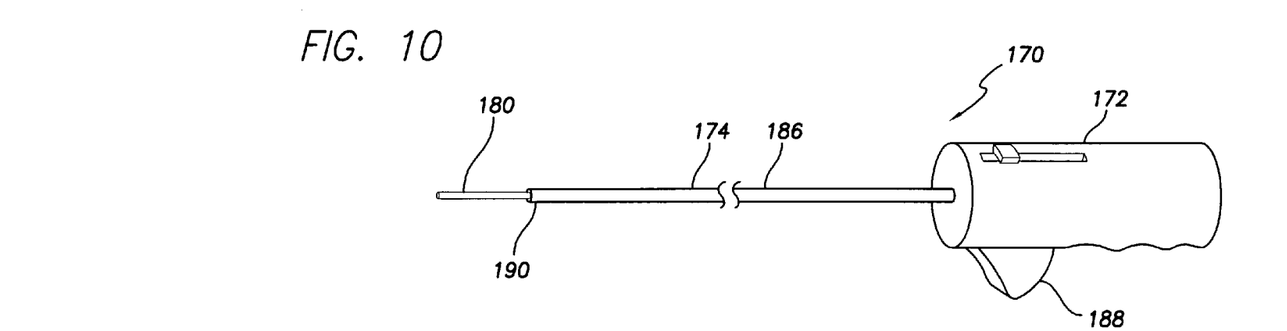
FIG. 10 is a perspective view of an assembly in accordance with another embodiment of the present invention comprising a guide wire and an actuator handle for deflecting a distal end of the guide wire.
Figure 11:
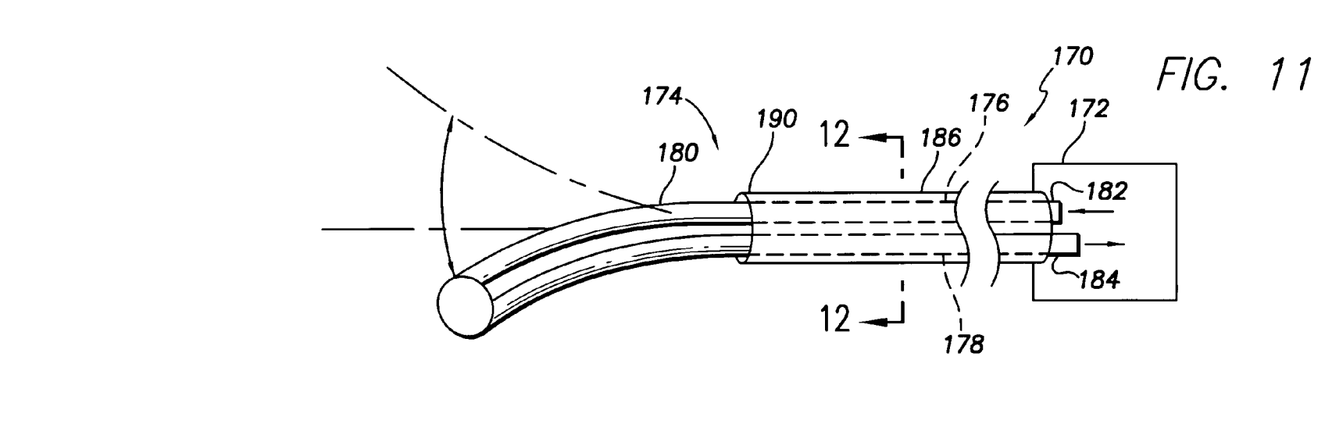
FIG. 11 is a side view of the assembly of FIG. 10, seen in simplified form, with a distal end of the guide wire in a deflected state.
Figure 12:
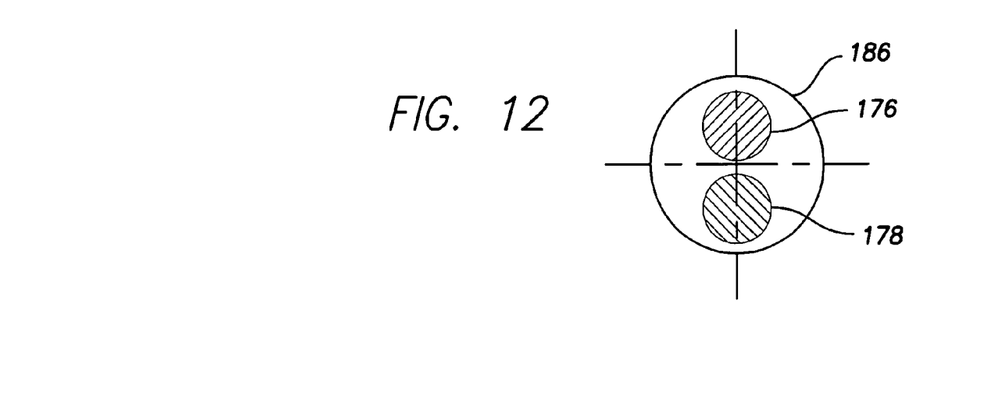
FIG. 12 is a transverse cross section view of the assembly of FIG. 11 as seen along the line 12-12 in FIG. 11.

With reference to FIGS. 10-12, there is shown an alternative embodiment of the invention comprising a guide wire assembly 170 including a handle 172 and a guide wire 174 extending therefrom. The guide wire 174 comprises first and second guide wire portions 176 and 178 and a distal end portion 180 that is deflectable by an actuating mechanism carried by the handle 172 and through which differential push-pull forces may be applied to proximal extremities 182 and 184 of the guide wire portions 176 and 178. This embodiment is similar to the previously described embodiments (FIGS. 3-9) except that the guide wire 174 includes an outer sheath 186 that may be slid longitudinally by means of a manually actuated lever 188 to control the length of the guide wire's distal end portion 180 that projects from a distal extremity 190 of the sheath 186. The sheath adds stiffness that resists deflection so that the exposed distal end portion 180 of the guide wire will be the region of greatest deflection. The sheath also keeps the wire portions 176 and 178 parallel, thus avoiding bowing along their lengths which might compromise the deflection function.

Figure 13:
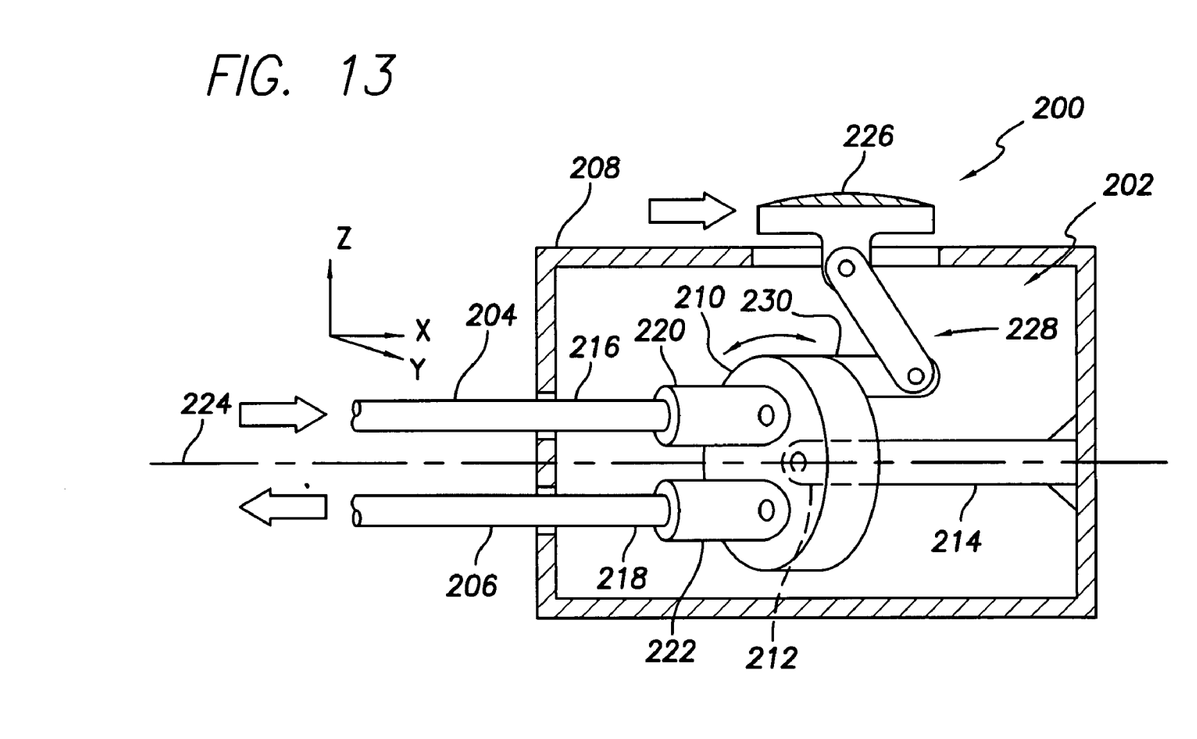
FIG. 13 is a perspective view of a portion of a mechanism forming part of an actuator for deflecting a distal end portion of a guide wire such as that shown in FIGS. 4-12.

With reference to FIG. 13, there is shown in schematic form portions of a handle 200 carrying a mechanism 202 for providing differential push-pull displacement of wire portions 204 and 206 of a guide wire such as shown in the above-described embodiments. It will be understood that the mechanism 202 shown in FIG. 13 is by way of example only; those skilled in the art will recognize alternate approaches, manual as well as power driven, to imparting the required differential displacement to the guide wire portions.

The handle 200 includes a housing 208 enclosing the mechanism 202 that comprises a pivotable member or plate 210 mounted to rock or rotate about the distal end 212 of a fixed pivot pin 214 secured to the housing 208. Attached to the plate 210 are proximal ends 216 and 218 of the guide wire portions 204 and 206, the attachment points 220 and 222 being disposed bilaterally of a longitudinal center line 224 along which the pivot pin 214 is disposed. The pivot plate 210 is thus disposed to rock about the distal end of the pivot pin 214 to cause differential displacements of the guide wire portions 204 and 206.

Also carried by the housing is a manually displaceable element, preferably in the form of a longitudinally slidable button 226 attached by a linkage 228 to the pivot plate 210 at a point 230 offset from the center line 224. Manually sliding the button 226 forward or backward by means of, for example, a user's thumb will cause the plate 210 to rock or rotate about the pivot pin 214 to differentially displace the guide wire portions 204 and 206 to thereby cause deflection of the distal end of the guide wire as already explained.

Figure 14:
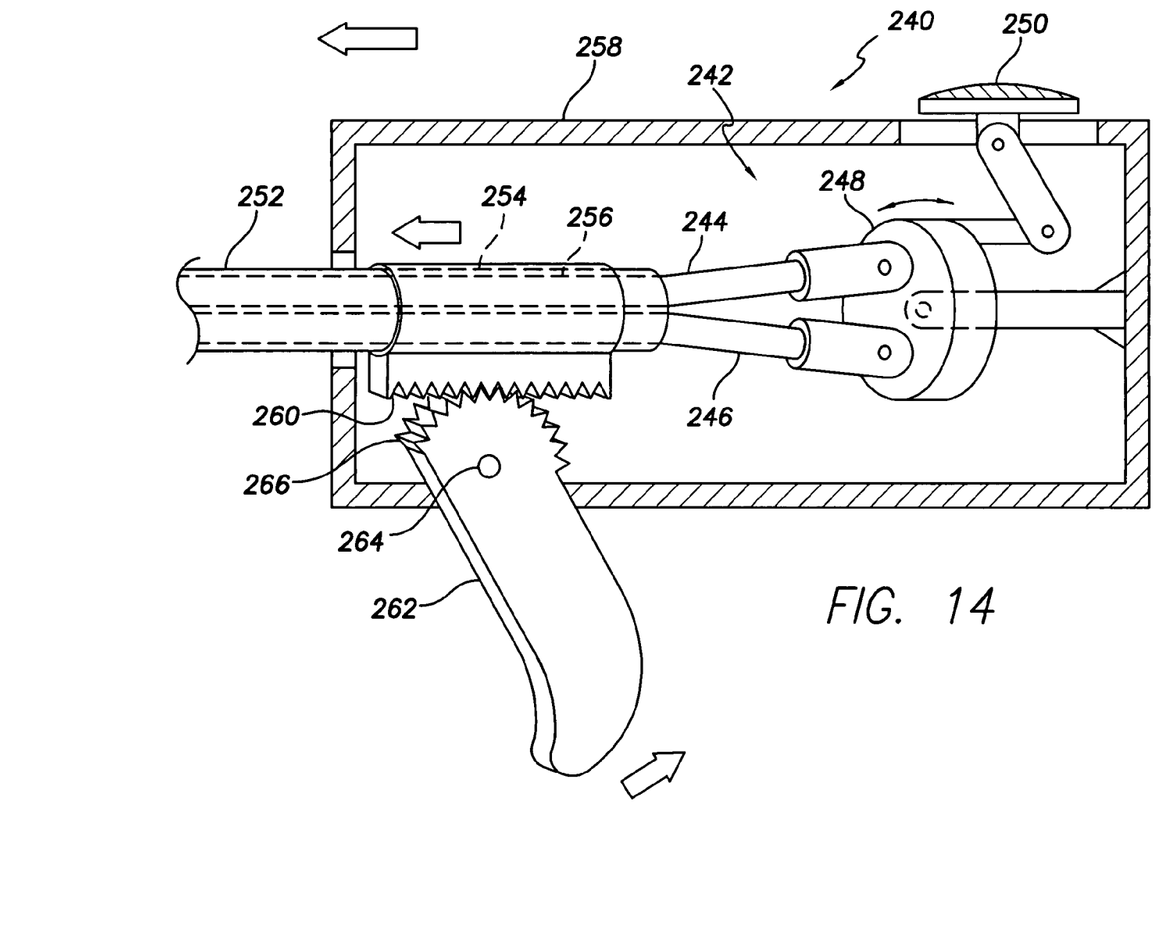
FIG. 14 is a perspective view of a portion of an actuator of the type that may be used with a guide wire assembly such as that shown in FIGS. 10 and 11.

Turning to FIG. 14, there is shown in schematic form portions of a guide wire handle 240 including a mechanism 242 such as that already described for imparting differential displacement of guide wire portions 244 and 246 by means of a pivot plate 248 in response to movement of a manually displaceable element such as a thumb button 250. The mechanism 242 of FIG. 14 further includes elements for longitudinally displacing a guide wire sheath 252 such as that used in the embodiments of FIGS. 10-12. Again, it should be noted that the mechanism shown in FIG. 14 is exemplary only and that it will be obvious to those skilled in the art that alternative mechanisms for displacing the various elements may be used instead.

The guide wire sheath 252 includes a proximal end 254 captured within, and secured to, a tubular member 256 mounted for linear longitudinal fore and aft motion within a housing 258 of the handle 240. The tubular member 256 carries a longitudinally extending gear rack 260. The handle 240 further carries a lever 262 pivotable about a pivot axis 264 fixed relative to the handle housing 258. The lever 262 includes a sector gear 266 in mesh with the gear rack 260 on the tubular member. It will thus be seen that the lever 262 and tubular member 256 define a rack and pinion drive for converting the rotary motion of the lever 262 about the pivot 264 to linear motion of the tubular member 256. The linear motion of the tubular member in turn controls the fore and aft longitudinal movement of the guide wire sheath 252 so as to control the extent that a distal end portion of the guide wire, such as the distal end portion 180 in FIGS. 10 and 11, is exposed from the distal extremity of the sheath 252.

Figure 15:
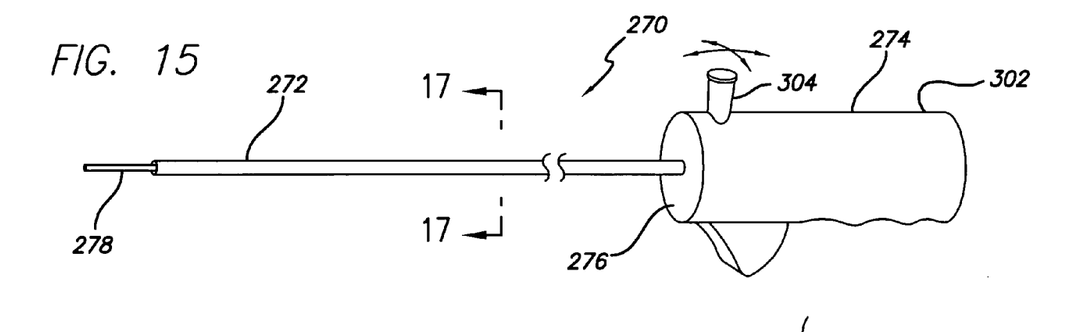
FIG. 15 is a perspective view of an assembly comprising the combination of a guide wire and guide wire actuator in accordance with yet another embodiment of the present invention in which a distal end of the guide wire is deflectable along two axes.
Figure 16:
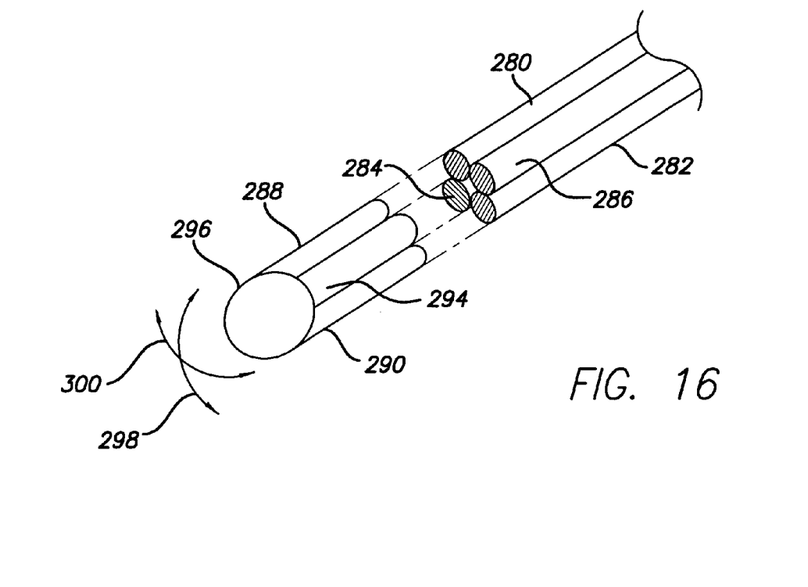
FIG. 16 is a simplified perspective view of the distal end of the guide wire forming part of the assembly of FIG. 15.
Figure 17:
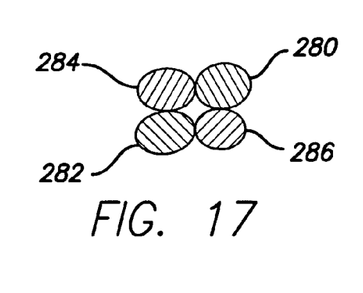
FIG. 17 is a cross section view as seen along the line 17-17 in FIG. 15.

With reference to FIGS. 15-17, there is shown in schematic form another exemplary embodiment of the invention comprising an assembly 270 having a guide wire 272 in combination with a guide wire deflection actuator handle 274 at a proximal end 276 of the guide wire.

The guide wire 272 comprises an elongated structure having a distal end portion 278. The guide wire comprises first, second, third and fourth wire portions 280, 282, 284 and 286, respectively, having distal extremities 288, 290, 292 and 294, and proximal extremities (not shown). The wire portions lie adjacent to each other along their lengths; they may be in abutting or near abutting relationship with each other. The distal extremities may be joined by, for example, a weld that preferably takes the form of a bead 296. As before, each of the wire portions may comprise wire formed of a biocompatible, biostable material such as stainless steel in accordance with one specific non-limiting example. Each of the wires preferably has sufficient column strength to transmit a longitudinally directed compressive force applied to the proximal extremity thereof. The overall diameter of the guide wire may be in the range of 0.012 to 0.016 inch in accordance with one example.

The use of at least three wire portions joined at their distal extremities makes possible deflection of the distal end portion of the guide wire along two axes effected by differential displacement of the wire portions. Accordingly, in the 4-wire portion embodiment of FIGS. 15-17, differential displacement of the wire portions 280 and 282 will deflect the distal end portion of the guide wire in a first direction 298, similar to that described in connection with the embodiments of FIGS. 3-9. Push-pull displacement of the remaining two wire portions 284 and 286 results in deflection of the distal end portion 278 of the guide wire in a second direction 300 generally perpendicular to the first direction. It will be evident that these two motions may be combined to deflect the distal end portion in both directions simultaneously for greater control in advancing and steering the distal end portion 278 of the guide wire through, for example, the vasculature of the coronary sinus region of the heart.

The handle 274 may include a housing 302 that may enclose a mechanism along the lines of that disclosed in FIG. 13 for imparting the desired deflection of the distal end portion 278 of the guide wire. Proximal extremities of the four guide wire portions would in such a case be pivotably attached to a pivot plate mounted to pivot about a pivot point in two directions instead of only a single direction by means of a knob 304 like that shown in FIG. 15.

Figure 18:
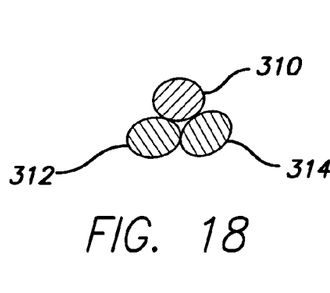
FIG. 18 is a cross section view of a guide wire in accordance with an alternative form of that depicted in FIGS. 15-17.

As already suggested, the two-axis guide wire 272 may comprise three guide wire portions 310, 312 and 314 instead of four, as shown schematically in FIG. 18. It will be equally evident that more than four guide wire portions may be employed.

Figure 19:
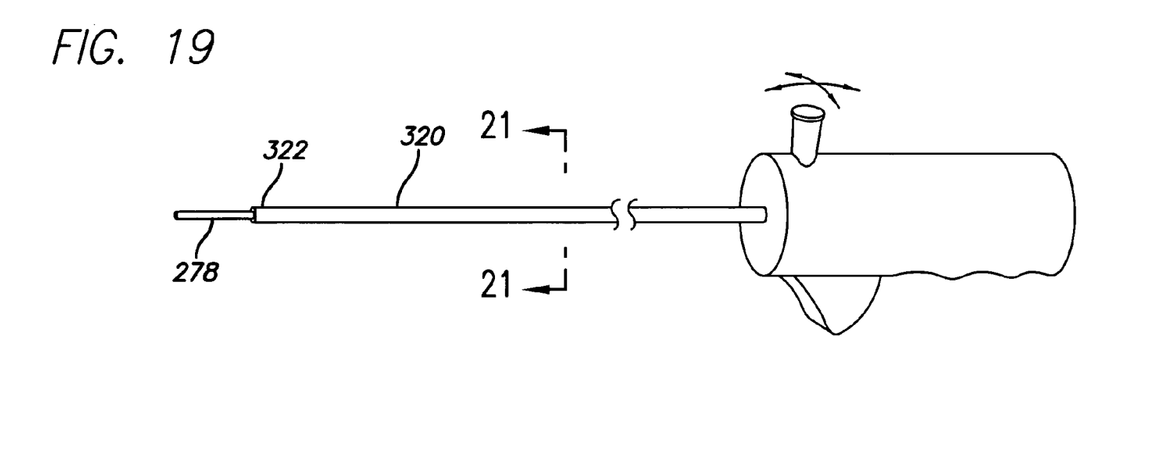
FIG. 19 is a perspective view of an assembly in accordance with another embodiment of the present invention comprising the combination of a guide wire and actuating handle.
Figure 20:
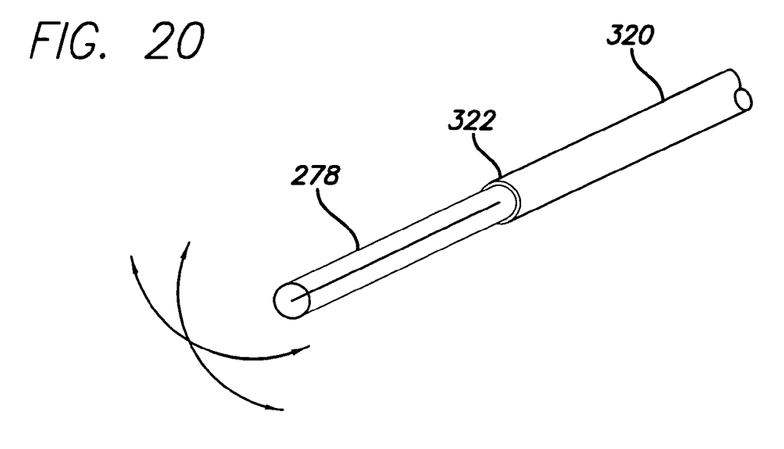
FIG. 20 is a perspective view of the distal end of the guide wire forming part of the assembly of FIG. 19.
Figure 21:
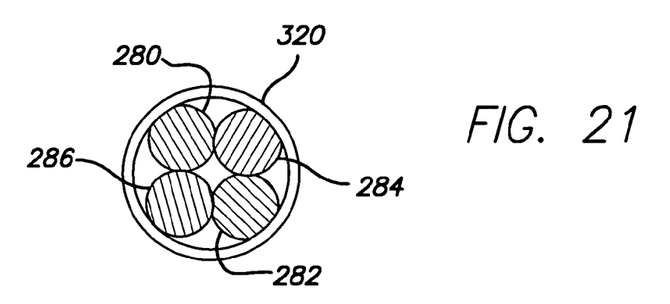
FIG. 21 is a cross section view of the assembly depicted in FIG. 19 as seen along the line 21-21 in FIG. 19.
Figure 22:
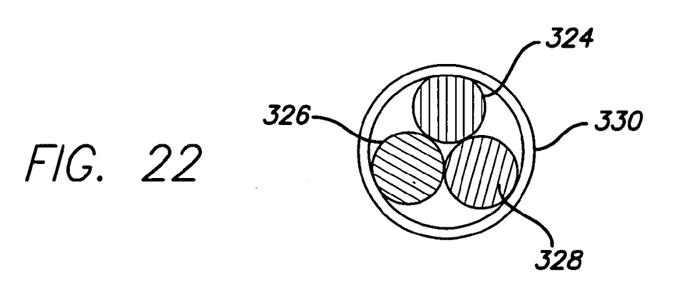
FIG. 22 is a cross section view of the assembly depicted in FIG. 19 of a guide wire in accordance with an alternative form of that depicted in FIGS. 19-21.

With reference to FIGS. 19-21, the guide wire 272 may include an outer sheath 320 that may be manually displaced forward or backward to control the length of the distal end portion 278 of the guide wire that is exposed beyond a distal extremity 322 of the sheath. As before, the retraction of the sheath 320 may be controlled by means of a lever-actuated rack and pinion drive along the lines of that disclosed in FIG. 14. FIG. 22 shows a further alternative embodiment wherein the guide wire 272 is formed of three guide wire portions 324, 326 and 328 instead of four such as that depicted in FIGS. 19-21. The three guide wire portions are enclosed within a sheath 330 having a distal extremity (not shown) from which a distal end portion of the guide wire projects to a greater or lesser extent in response to the manipulation of an actuating mechanism such as that shown in FIG. 14.

Figure 23:
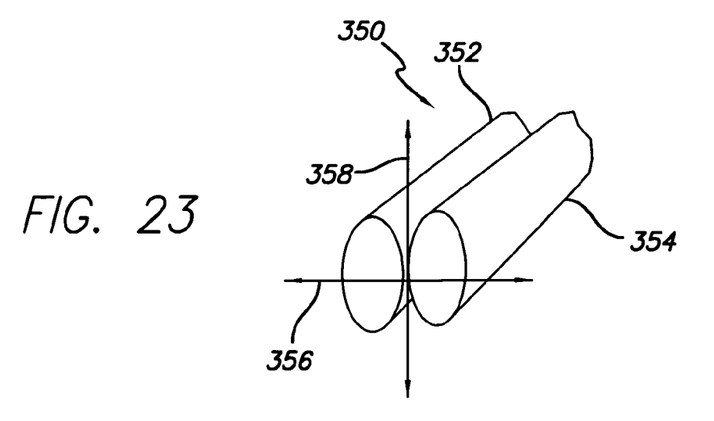
FIG. 23 is a perspective view of a portion of a guide wire in accordance with another embodiment of the invention comprising a pair of side-by-side wire portions, each having an elliptical cross section.
Figure 24:
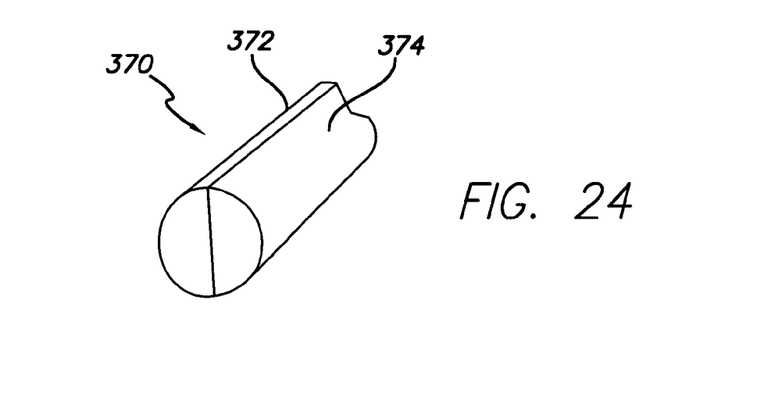
FIG. 24 is a perspective view of a portion of a guide wire in accordance with yet another embodiment of the invention in which the guide wire comprises a two-part segmented structure.
Figure 25:
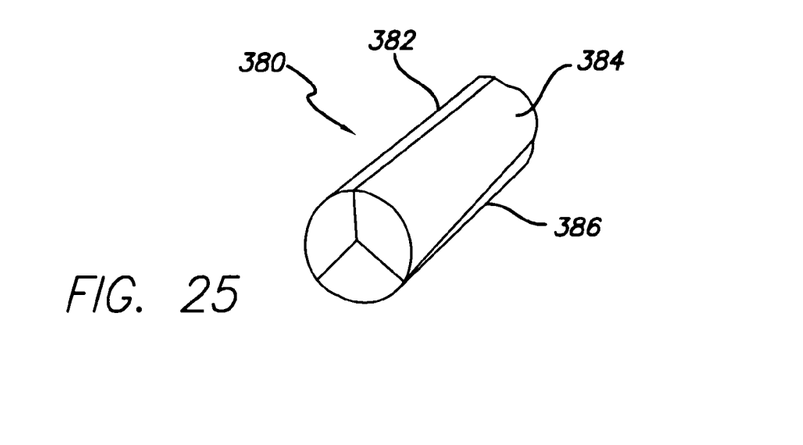
FIG. 25 is a perspective view of a portion of a guide wire in accordance with still another embodiment of the invention in which the guide wire comprises a three-part segmented structure.

With reference to FIGS. 23-25, depicted schematically are guide wires in accordance with alternative embodiments of the invention.

FIG. 23 shows a portion of a guide wire 350 along the lines of that shown in FIGS. 3-5, comprising two side-by-side guide wire portions 352 and 354, each having a generally elliptical cross section. This shape provides the guide wire 350 with greater flexibility and therefore greater deflection along a direction 356 paralleling the major axes of those sections. It will be evident that other non-circular cross sections may be employed to obtain a desired differential in directional deflection of the guide wire in response to differential displacements of the guide wire portions.

FIGS. 24 and 25 show portions of guide wires segmented to define guide wire portions arranged so as to provide the guide wires with compact cross sectional areas while facilitating deflection and steerability. FIG. 24 illustrates a portion of a guide wire 370 of circular cross section comprising two back-to-back guide wire portions 372 and 374 each having a semi-circular cross section shape. FIG. 25 shows a portion of a guide wire 380, again having a circular cross section, but in this case segmented to form three guide wire portions 382, 384 and 386 each subtending 120° of arc in cross section. Deflection of the guide wire 380 along two axes may thereby be provided, as previously explained. It will be apparent that the segments of the guide wire need not be identical in cross section, and that more than three segmented guide wire portions may be provided.

The guide wires of FIGS. 23-25 may comprise any of the features previously described, including the various techniques for joining the distal extremities of the guide wire portions, the inclusion of a sheath about the guide wire portions, the actuating mechanisms, and so forth.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. A guide wire assembly for facilitating placement of a medical device, the assembly comprising:

a longitudinally extending guide wire comprising a plurality of wire portions disposed adjacent to each other, each of the plurality of wire portions having a distal extremity and a proximal extremity, the distal extremities of the plurality of wire portions being joined, each of the plurality of wire portions having an outer surface extending from the distal extremity to the proximal extremity, a substantial longitudinal length of the outer surfaces of the plurality of wire portions are configured to abut each other; and an actuator operatively associated with the proximal extremities of the plurality of wire portions for applying longitudinally directed, differential push-pull forces to said proximal extremities for deflecting a distal end portion of the guide wire.

2. The assembly of claim 1 wherein:
the distal extremities of the plurality of wire portions are joined by a weld.

3. The assembly of claim 1 wherein:
the distal extremities of the plurality of wire portions are joined by a cap encapsulating said distal extremities.

4. The assembly of claim 1 wherein:
the distal extremities of the plurality of wire portions are joined by means of a filament wound about the distal extremities.

5. The assembly of claim 1 wherein:
the actuator comprises a pivotable member operatively associated with the proximal extremities of the plurality of wire portions for applying said push-pull forces.

6. The assembly of claim 1 further comprising:
a sheath disposed about said guide wire, the deflectable distal end portion of the guide wire projecting from a distal extremity of the sheath.

7. The assembly of claim 1 wherein:
the plurality of wire portions comprise at least two wire portions.

8. The assembly of claim 1 wherein:
each wire portion of the plurality of wire portions has a non-circular cross section, wherein the wire portions provide differential deflections of the distal end portion of the guide wire along different deflection axes.

9. The assembly of claim 1 wherein:
the guide wire is segmented in cross section to define the plurality of wire portions.

10. The assembly of claim 1 wherein:
the plurality of wire portions have a combined circular cross sectional shape.

11. A guide wire assembly for facilitating placement of a medical device, the assembly comprising:
a guide wire comprising (a) a first longitudinally extending wire portion having an outer surface extending from a distal extremity to a proximal extremity and (b) a second longitudinally extending wire portion having an outer surface extending from a distal extremity to a proximal extremity, said second wire portion being disposed adjacent to said first wire portion such that the outer surface of the first longitudinally extending wire portion abuts the outer surface of the second longitudinally extending wire portion throughout a substantial longitudinal length of the first and second wire portions, the distal extremities of the first and second wire portions being joined; and an actuator operatively associated with the proximal extremities of the first and second wire portions for applying longitudinally directed, differential push-pull forces to the proximal extremities of said first and second wire portions for deflecting a distal end portion of the guide wire.

12. The assembly of claim 11 wherein:
the distal extremities of the first and second wire portions are joined by a weld.

13. The assembly of claim 11 wherein:
the distal extremities of the first and second wire portions are joined by a cap encapsulating said distal extremities.

14. The assembly of claim 11 wherein:
the distal ends of the first and second wire portions are joined by means of a filament wound about the distal extremities.

15. The assembly of claim 11 wherein:
the first and second wire portions comprise sections of a single wire, the joinder of the distal extremities of said wires comprising a bend in said single wire.

16. The assembly of claim 11 further comprising:
a sheath disposed about said guide wire, the distal end portion of the guide wire projecting from a distal extremity of the sheath.

17. The assembly of claim 16 wherein:
the sheath is movable along the length of the guide wire to control the length of the distal end portion of the guide wire projecting from the distal extremity of the sheath.

18. The assembly of claim 11 wherein:
the actuator comprises a pivotable member operatively associated with the proximal extremities of the plurality of wire portions for applying said push-pull forces.

19. The assembly of claim 11 wherein:
each of the first and second wire portion has a semicircular cross section, and the combined cross section of the first and second wire portion is circular.

* * * * *